US007267969B2

(12) United States Patent
Pannuri et al.

(10) Patent No.: US 7,267,969 B2
(45) Date of Patent: Sep. 11, 2007

(54) THERMOSTABLE OMEGA-TRANSAMINASES

(75) Inventors: Sachin Pannuri, Scotch Plains, NJ (US); Sanjay Venkatesh Kamat, Kendall Park, NJ (US); Abraham Rogelio Martin Garcia, Houghton, MI (US)

(73) Assignee: Cambrex Karlskoga, Karlskoga (SE)

( * ) Notice: Subject to any disclaimer, the term of this patent is extended or adjusted under 35 U.S.C. 154(b) by 0 days.

(21) Appl. No.: 11/627,995

(22) Filed: Jan. 29, 2007

(65) Prior Publication Data

US 2007/0134769 A1 Jun. 14, 2007

Related U.S. Application Data

(62) Division of application No. 11/295,696, filed on Dec. 7, 2005, now Pat. No. 7,172,885.

(60) Provisional application No. 60/634,526, filed on Dec. 10, 2004.

(51) Int. Cl.

| | |
|---|---|
| ***C12P 13/00*** | (2006.01) |
| ***C12P 21/06*** | (2006.01) |
| ***C12P 9/10*** | (2006.01) |
| ***C12P 41/00*** | (2006.01) |
| ***C12N 9/06*** | (2006.01) |
| ***C07H 21/04*** | (2006.01) |

(52) U.S. Cl. .................... 435/128; 435/69.1; 435/191; 435/193; 435/280; 536/23.2

(58) Field of Classification Search .................... None
See application file for complete search history.

(56) References Cited

U.S. PATENT DOCUMENTS

| | | | | |
|---|---|---|---|---|
| 4,950,606 | A * | 8/1990 | Stirling et al. | 435/280 |
| 5,300,437 | A * | 4/1994 | Stirling et al. | 435/280 |
| 5,346,828 | A * | 9/1994 | Stirling et al. | 435/280 |
| 6,413,752 | B1 | 7/2002 | Takashima | |
| 6,727,083 | B2 | 4/2004 | Takashima | |
| 2005/0009015 | A1 | 1/2005 | Chase | |

OTHER PUBLICATIONS

Shin et al., "Asymmetric synthesis of chiral amines with omega-transaminase," *Biotechnol. Bioengin.* 65, 206-11, 1999.

Shin & Kim, "Comparison of the ω-Transamines from Different Microorganisms and Application to Production of Chiral Amines," *Biosci. Biotechnol. Biochem.* 65, 1782-88, 2001.

* cited by examiner

*Primary Examiner*—Rebecca E. Prouty
*Assistant Examiner*—Ganapathirama Raghu
(74) *Attorney, Agent, or Firm*—Banner & Witcoff, Ltd

(57) ABSTRACT

Thermostable omega-transaminases, particularly thermostable omega-transaminases which have a high reaction rate and which are tolerant to high concentrations of donor amine, can be used to enrich enantiomerically a mixture of chiral amines or to synthesize stereoselectively one of a pair of chiral amines in which the amino group is bound to a non-terminal, chirally substituted, carbon atom.

13 Claims, 4 Drawing Sheets

R[CNB05-01]= 0.4132 mM/min
R[CNB03-03]= 0.2556 mM/min

SEQUENCE LISTING

```
<160> NUMBER OF SEQ ID NOS: 18

<210> SEQ ID NO 1
<211> LENGTH: 1431
<212> TYPE: DNA
<213> ORGANISM: Arthrobacter citreus
<220> FEATURE:
<223> OTHER INFORMATION: Cel9611

<400> SEQUENCE: 1

atgggtttaa cagtgcaaaa aataaactgg gagcaagtta aagaatggga tcgtaaatac      60

ctgatgagga cgtttagtac ccaaaatgag tatcaacctg taccgattga atcaacagaa     120

ggtgactatt tgattatgcc tgatggcaca agattattag atttcttcaa tcaactttat     180

tgtgtcaatt taggccagaa aaatcaaaaa gttaatgctg caatcaagga ggctttagac     240

cgatatggtt ttgtatggga tacttatgca actgattata aagccaaagc agccaagata     300

attattgagg atattttagg tgatgaagac tggccaggaa aagttaggtt cgtatcaaca     360

ggaagtgaag cagtggaaac ggcactgaat atcgcgaggt tatatacaaa tcgcccacta     420

gtggttacac gagaacacga ttatcatggt tggactggtg gagctgctac tgttactcga     480

ttaaggtcat atcgaagtgg tttagttggg gaaaattcag aatctttttc agcacaaata     540

cccggttcat catataatag tgctgttttg atggcgccat cccctaacat gtttcaggat     600

tcgaacggca actgcctaaa agatgaaaac ggggaattgt tgagtgtaaa gtatacacgt     660

cgtatgatcg aaaactatgg tccggaacaa gtggcagcag tgataactga agtatcgcaa     720

ggtgcaggct ctgctatgcc cccatatgaa tacattccac aattccgaaa aatgacaaaa     780
```

-continued

```
gaactaggtg tcctttggat taatgatgaa gttcttactg gctttgggcg tacagggaag    840

tggtttggat atcagcatta tggggtacag ccagatataa tcactatggg taaaggactc    900

tccagttcct cactccctgc tggcgctgtc gtagttagta aggaaattgc agcgtttatg    960

gataagcacc gatgggagtc agtatccacc tatgctggtc atccagttgc gatggctgcg   1020

gtttgtgcaa atttagaagt aatgatggaa gaaaaccttg ttgagcaagc gaagaacagc   1080

ggcgagtata taaggagtaa acttgaactt ctgcaagaaa agcataaaag tataggcaat   1140

ttcgacggat atggcctttt atggatagta gatattgtga atgccaagac taagactcct   1200

tacgtaaaat tggacaggaa ctttacgcac gggatgaatc caaatcaaat cccaacacaa   1260

atcattatga aaaaagcgct agaaaaagga gtgctgattg gtggagtaat gcctaataca   1320

atgagaattg gcgcatcttt gaatgttagt cgcggagaca tcgataaagc aatggatgca   1380

ctggattatg cacttgacta tttagaaagt ggagaatggc agcaatccta a            1431
```

```
<210> SEQ ID NO 2
<211> LENGTH: 476
<212> TYPE: PRT
<213> ORGANISM: Arthrobacter citreus
<220> FEATURE:
<223> OTHER INFORMATION: Cel9611

<400> SEQUENCE: 2

Met Gly Leu Thr Val Gln Lys Ile Asn Trp Glu Gln Val Lys Glu Trp
 1               5                  10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Asp
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Tyr Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Pro Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Ala Gly Ser Ala Met Pro Pro Tyr Glu Tyr Ile Pro Gln Phe Arg
```

-continued

```
                245                 250                 255

Lys Met Thr Lys Glu Leu Gly Val Leu Trp Ile Asn Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Thr His Gly Met Asn Pro Asn Gln
                405                 410                 415

Ile Pro Thr Gln Ile Ile Met Lys Lys Ala Leu Glu Lys Gly Val Leu
            420                 425                 430

Ile Gly Gly Val Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475
```

<210> SEQ ID NO 3
<211> LENGTH: 1431
<212> TYPE: DNA
<213> ORGANISM: Arthrobacter citreus
<220> FEATURE:
<223> OTHER INFORMATION: mutant transaminase

<400> SEQUENCE: 3

```
atgggtttaa cagtgcaaaa aataaactgg gagcaagtta aagaatggga tcgtaaatac     60

ctgatgagga cgtttagtac ccaaaatgag tatcaacctg taccgattga atcaacagaa    120

ggtgactatt tgattatgcc tggtggcaca agattattag atttcttcaa tcaactttat    180

tgtgtcaatt taggccagaa aaatcaaaaa gttaatgctg caatcaagga ggctttagac    240

cgatatggtt ttgtatggga tacttatgca actgattata aagccaaagc agccaagata    300

attattgagg atattttagg tgatgaagac tggccaggaa aagttaggtt cgtatcaaca    360

ggaagtgaag cagtggaaac ggcactgaat atcgcgaggt tatatacaaa tcgcccacta    420

gtggttacac gagaacacga ttatcatggt tggactggtg gagctgctac tgttactcga    480

ttaaggtcat atcgaagtgg tttagttggg gaaaattcag aatctttttc agcacaaata    540

cccggttcat catataatag tgctgttttg atggcgccat cccctaacat gtttcaggat    600

tcgaacggca actgcctaaa agatgaaaac ggggaattgt tgagtgtaaa gtatacacgt    660

cgtatgatcg aaaactatgg tccggaacaa gtggcagcag tgataactga agtatcgcaa    720

ggtgtaggct ctactatgcc cccatatgaa tacattccac aattccgaaa aatgacaaaa    780
```

-continued

```
gaactaggtg tcctttggat taatgatgaa gttcttactg gctttgggcg tacagggaag    840

tggtttggat atcagcatta tggggtacag ccagatataa tcactatggg taaaggactc    900

tccagttcct cactccctgc tggcgctgtc gtagttagta aggaaattgc agcgtttatg    960

gataagcacc gatgggagtc agtatccacc tatgctggtc atccagttgc gatggctgcg   1020

gtttgtgcaa atttagaagt aatgatggaa gaaaaccttg ttgagcaagc gaagaacagc   1080

ggcgagtata taaggagtaa acttgaactt ctgcaagaaa agcataaaag tataggcaat   1140

ttcgacggat atggcctttt atggatagta gatattgtga atgccaagac taagactcct   1200

tacgtaaaat tggacaggaa ctttacgcac gggatgaatc caaatcaaat cccgacacaa   1260

atcattatga aaaaagcgct agaaaaagga gtgctgattg gtggagtaat gcctaataca   1320

atgagaattg gcgcatcttt gaatgttagt cgcggagaca tcgataaagc aatggatgca   1380

ctggattatg cacttgacta tttagaaagt ggagaatggc agcaatccta a            1431
```

<210> SEQ ID NO 4
<211> LENGTH: 476
<212> TYPE: PRT
<213> ORGANISM: Arthrobacter citreus
<220> FEATURE:
<223> OTHER INFORMATION: mutant transaminase

<400> SEQUENCE: 4

```
Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Tyr Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Tyr Arg Ser Gly Leu Val Gly Glu Asn Ser Glu Ser Phe
                165                 170                 175

Ser Ala Gln Ile Pro Gly Ser Ser Tyr Asn Ser Ala Val Leu Met Ala
            180                 185                 190

Pro Ser Pro Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Ile Pro Gln Phe Arg
```

-continued

```
                245                 250                 255

Lys Met Thr Lys Glu Leu Gly Val Leu Trp Ile Asn Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Thr His Gly Met Asn Pro Asn Gln
                405                 410                 415

Ile Pro Thr Gln Ile Ile Met Lys Lys Ala Leu Glu Lys Gly Val Leu
            420                 425                 430

Ile Gly Gly Val Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475
```

```
<210> SEQ ID NO 5
<211> LENGTH: 1431
<212> TYPE: DNA
<213> ORGANISM: Arthrobacter citreus
<220> FEATURE:
<223> OTHER INFORMATION: mutant transaminase Chir9867

<400> SEQUENCE: 5

atgggtttaa cagtgcaaaa aataaactgg gagcaagtta aagaatggga tcgtaaatac      60

ctgatgagga cgtttagtac ccagaacgag tatcaacctg taccgattga atcaacagaa     120

ggtgactatt tgattatgcc tgatggcaca agattattag atttcttcaa tcaactttgt     180

tgtgtcaatt taggccagaa aaatcaaaaa gttaatgctg caatcaagga ggctttagac     240

cgatatggtt ttgtatggga tacttatgca actgattata aagccaaagc agccaagata     300

attattgagg atattttagg tgatgaagac tggccaggaa aagttaggtt cgtatcaaca     360

ggaagtgaag cagtggaaac ggcactgaat atcgcgaggt tatatacaaa tcgcccacta     420

gtagttacac gagaacacga ttatcatggt tggactggtg gagctgctac tgttactcga     480

ttaaggtcat ttcgaagtgg tttagttggg gaaaattcag aatctttttc agcacaaata     540

cctggttcat catatagtag tgctgttttg atggcgccat cccctaacat gtttcaggat     600

tcgaacggca actgcctaaa agatgaaaac ggggaattgt tgagtgtaaa gtatacacgt     660

cgtatgatcg aaaactatgg tccggaacaa gtggcagcag tgataactga agtatcgcaa     720

ggtgtaggct ctactatgcc cccatatgaa tacgttccac aaatccgaaa aatgacaaaa     780
```

-continued

```
gaactaggtg tcctttggat tagtgatgaa gttcttactg gctttgggcg tacagggaag    840

tggtttggat atcagcatta tggggtacag ccagatataa tcactatggg taaaggactc    900

tccagttcct cactccctgc tggcgctgtc gtagttagta aggaaattgc agcgtttatg    960

gataagcacc gatgggagtc agtatccacc tatgctggtc atccagttgc gatggctgcg   1020

gtttgtgcaa atttagaagt aatgatggaa gaaaaccttg ttgagcaagc gaagaacagc   1080

ggcgagtata taaggagtaa acttgaactt ctgcaagaaa agcataaaag tataggcaat   1140

ttcgacggat atggcctttt atggatagtt gatattgtga atgccaagac taagactcct   1200

tacgtaaaat tggacaggaa ctttaggcac gggatgaatc caaatcaaat cccgacacaa   1260

atcattatgg aaaaagcgct agaaaaagga gtgctgattg gtggagcaat gcctaataca   1320

atgagaattg gtgcatcttt gaatgttagt cgcggagaca tcgataaagc aatggatgca   1380

ctggattatg cacttgacta tctagaaagt ggagaatggc agcaatccta a            1431
```

<210> SEQ ID NO 6
<211> LENGTH: 476
<212> TYPE: PRT
<213> ORGANISM: Arthrobacter citreus
<220> FEATURE:
<223> OTHER INFORMATION: mutant transaminase Chir9867

<400> SEQUENCE: 6

```
Met Gly Leu Thr Val Gln Lys Ile Asn Trp Glu Gln Val Lys Glu Trp
1               5                   10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Asp
        35                  40                  45

Gly Thr Arg Leu Leu Asp Phe Phe Asn Gln Leu Cys Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Ser Ser Ala Val Leu Met Ala
            180                 185                 190

Pro Ser Pro Asn Met Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Val Pro Gln Ile Arg
```

-continued

```
            245                 250                 255

Lys Met Thr Lys Glu Leu Gly Val Leu Trp Ile Ser Asp Glu Val Leu
        260                 265                 270

Thr Gly Phe Gly Arg Thr Gly Lys Trp Phe Gly Tyr Gln His Tyr Gly
    275                 280                 285

Val Gln Pro Asp Ile Ile Thr Met Gly Lys Gly Leu Ser Ser Ser Ser
290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475


<210> SEQ ID NO 7
<211> LENGTH: 1431
<212> TYPE: DNA
<213> ORGANISM: Arthrobacter citreus
<220> FEATURE:
<223> OTHER INFORMATION: mutant transaminase CNB03-01

<400> SEQUENCE: 7

atgggtttaa cagtgcaaaa aataaactgg gagcaagtta aagaatggga tcgtaaatac      60

ctgatgagga cgtttagtac ccagaacgag tatcaacctg taccgattga atcaacagaa     120

ggtgactatt tgattatgcc tggtggcaca agattattag atttcttcaa tcaactttgt     180

tgtgtcaatt taggccagaa aaatcaaaaa gttaatgctg caatcaagga ggctttagac     240

cgatatggtt ttgtatggga tacttatgca actgattata aagccaaagc agccaagata     300

attattgagg atattttagg tgatgaagac tggccaggaa aagttaggtt cgtatcaaca     360

ggaagtgaag cagtggaaac ggcactgaat atcgcgaggt tatatacaaa tcgcccacta     420

gtggttacac gagaacacga ttatcatggt tggactggtg gagctgctac tgttactcga     480

ttaaggtcat ttcgaagtgg tttagttggg gaaaattcag aatctttttc agcacaaata     540

cctggctcat catatagtag tgctgttttg atggcgccat cctctaacac gtttcaggat     600

tcgaacggca actgcctaaa agatgaaaac ggggaattgt tgagtgtaaa gtatacacgt     660

cgtatgatcg aaaactatgg tccggaacaa gtggcagcag tgataactga agtatcgcaa     720

ggtgtaggct ctactatgcc cccatatgaa tacgttccac aaatccgaaa aatgacaaaa     780
```

```
gaactaggtg tcctttggat tagtgatgaa gttcttactg gctttgggcg tacagggaag    840

tggtttggat atcagcatta tggggtacag ccagatataa tcactatggg taaaggactc    900

tccagttcct cactccctgc tggcgctgtc gtagttagta aggaaattgc agcgtttatg    960

gataagcacc gatgggagtc agtatccacc tatgctggtc atccagttgc gatggctgcg   1020

gtttgtgcaa atttagaagt aatgatggaa gaaaaccttg ttgagcaagc gaagaacagc   1080

ggcgagtata taaggagtaa acttgaactt ctgcaagaaa agcataaaag tataggcaat   1140

ttcgacggat atggcctttt atggatagtt gatattgtga atgccaagac taagactcct   1200

tacgtaaaat tggacaggaa ctttaggcac gggatgaatc caaatcaaat cccgacacaa   1260

atcattatga aaaaagcgct agaaaaagga gtgctgattg gtggagcaat gcctaataca   1320

atgagaattg gtgcatcttt gaatgttagt cgcggagaca tcgataaagc aatggatgca   1380

ctggattatg cacttgacta tctagaaagt ggagaatggc agcaatccta a            1431
```

```
<210> SEQ ID NO 8
<211> LENGTH: 476
<212> TYPE: PRT
<213> ORGANISM: Arthrobacter citreus
<220> FEATURE:
<223> OTHER INFORMATION: mutant transaminase CNB03-01

<400> SEQUENCE: 8

Met Gly Leu Thr Val Gln Lys Ile Asn Trp Glu Gln Val Lys Glu Trp
 1               5                  10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Cys Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Ser Ser Ala Val Leu Met Ala
            180                 185                 190

Pro Ser Ser Asn Thr Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Val Pro Gln Ile Arg
```

-continued

```
                245                 250                 255

Lys Met Thr Lys Glu Leu Gly Val Leu Trp Ile Ser Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475


<210> SEQ ID NO 9
<211> LENGTH: 1431
<212> TYPE: DNA
<213> ORGANISM: Arthrobacter citreus
<220> FEATURE:
<223> OTHER INFORMATION: mutant transaminase CNB03-02

<400> SEQUENCE: 9

atgggtttaa cagtgcaaaa aataaactgg gagcaagtta aagaatggga tcgtaaatac      60

ctgatgagga cgtttagtac ccagaacgag tatcaacctg taccgattga atcaacagaa     120

ggtgactatt tgattatgcc tggtggcaca agattattag atttcttcaa tcaactttgt     180

tgtgtcaatt taggccagaa aaatcaaaaa gttaatgctg caatcaagga ggctttagac     240

cgatatggtt ttgtatggga tacttatgca actgattata aagccaaagc agccaagata     300

attattgagg atattttagg tgatgaagac tggccaggaa aagttaggtt cgtatcaaca     360

ggaagtgaag cagtggaaac ggcactgaat atcgcgaggt tatatacaaa tcgcccacta     420

gtggttacac gagaacacga ttatcatggt tggactggtg gagctgctac tgttactcga     480

ttaaggtcat ttcgaagtgg tttagttggg gaaaattcag aatctttttc agcacaaata     540

cctggctcat catatagtag tgctgttttg atggcgccat cctctaacac gtttcaggat     600

tcgaacggca actgcctaaa agatgaaaac ggggaattgt tgagtgtaaa gtatacacgt     660

cgtatgatcg aaaactatgg tccggaacaa gtggcagcag tgataactga agtatcgcaa     720

ggtgtaggct ctactatgcc cccatatgaa tacgttccac aaatccgaaa aatgacaaaa     780
```

-continued

```
gaactaggtg tcctttggat tagtgatgaa gttcttactg gctttgggcg tacagggaag    840

tggtttggat atcagcatta tggggtacag ccagatataa tcactatggg taaaggactc    900

tccagttcct cactccctgc tggcgctgtc gtagttagta aggaaattgc agcgtttatg    960

gataagcacc gatgggagtc agtatccacc tatgctggtc atccagttgc gatggctgcg   1020

gtttgtgcaa atttagaagt aatgatggaa gaaaaccttg ttgagcaagc gaagaacagc   1080

ggcgagtata taaggagtaa acttgaactt ctgcaagaaa agcataaaag tataggcaat   1140

ttcgacggat atggcctttt atggatagtt gatattgtga atgccaagac taagactcct   1200

tacgtaaaat tggacaggaa ctttaggcac gggatgaatc caaatcaaat cccgacacaa   1260

atcattatga aaaaagcgct agaaaaagga gtgctgattg gtggagcaat gcctaataca   1320

atgagaattg gtgcatcttt gaatgttagt cgcggagaca tcgataaagc aatggatgca   1380

ctggattatg cacttgacta tctagaaagt ggagaatggc agcaatccta a            1431
```

```
<210> SEQ ID NO 10
<211> LENGTH: 476
<212> TYPE: PRT
<213> ORGANISM: Arthrobacter citreus
<220> FEATURE:
<223> OTHER INFORMATION: mutant transaminase CNB03-02

<400> SEQUENCE: 10

Met Gly Leu Thr Val Gln Lys Ile Asn Trp Glu Gln Val Lys Glu Trp
 1               5                  10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Met Pro Gly
        35                  40                  45

Gly Thr Arg Leu Leu Asp Phe Phe Asn Gln Leu Cys Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Ser Ser Ala Val Leu Met Ala
            180                 185                 190

Pro Ser Ser Asn Thr Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Val Pro Gln Ile Arg
```

-continued

```
                245                 250                 255

Lys Met Thr Lys Glu Leu Gly Val Leu Trp Ile Ser Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Lys Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475


<210> SEQ ID NO 11
<211> LENGTH: 1431
<212> TYPE: DNA
<213> ORGANISM: Arthrobacter citreus
<220> FEATURE:
<223> OTHER INFORMATION: mutant transaminase CNB03-03

<400> SEQUENCE: 11

atgggtttaa cagtgcaaaa aataaactgg gagcaagtta aagaatggga tcgtaaatac      60

ctgatgagga cgtttagtac ccagaacgag tatcaacctg taccgattga atcaacagaa     120

ggtgactatt tgattacgcc tggtggcaca agattattag atttcttcaa tcaactttgt     180

tgtgtcaatt taggccagaa aaatcaaaaa gttaatgctg caatcaagga ggctttagac     240

cgatatggtt ttgtatggga tacttatgca actgattata aagccaaagc agccaagata     300

attattgagg atattttagg tgatgaagac tggccaggaa aggttaggtt cgtatcaaca     360

ggaagtgaag cagtggaaac ggcactgaat atcgcgaggt tatatacaaa tcgcccacta     420

gtggttacac gagaacacga ttatcatggt tggactggtg gagctgctac tgttactcga     480

ttaaggtcat ttcgaagtgg tttagttggg gaaaattcag aatctttttc agcacaaata     540

cctggctcat catatagtag tgctgttttg atggcgccat cctctaacac gtttcaggat     600

tcgaacggca actgcctaaa agatgaaaac ggggaattgt tgagtgtaaa gtatacacgt     660

cgtatgatcg aaaactatgg tccggaacaa gtggcagcag tgataactga agtatcgcaa     720

ggtgtaggct ctactatgcc cccatatgaa tacgttccac aaatccgaaa aatgacaaaa     780
```

```
gaactaggtg tcctttggat tagtgatgaa gttcttactg gctttgggcg tacagggaag    840

tggtttggat atcagcatta tggggtacag ccagatataa tcactatggg taaaggactc    900

tccagttcct cactccctgc tggcgctgtc gtagttagta aggaaattgc agcgtttatg    960

gataagcacc gatgggagtc agtatccacc tatgctggtc atccagttgc gatggctgcg   1020

gtttgtgcaa atttagaagt aatgatggaa gaaaaccttg ttgagcaagc gaagaacagc   1080

ggcgagtata taaggagtaa acttgaactt ctgcaagaaa agcataaaag tataggcaat   1140

ttcgacggat atggcctttt atggatagtt gatattgtga atgccaagac taagactcct   1200

tacgtaaaat tggacaggaa ctttaggcac gggatgaatc caaatcaaat cccgacacaa   1260

atcattatgg aaaaagcgct agaaaaagga gtgctgattg gtggagcaat gcctaataca   1320

atgagaattg gtgcatcttt gaatgttagt cgcggagaca tcgataaagc aatggatgca   1380

ctggattatg cacttgacta tctagaaagt ggagaatggc agcaatccta a             1431
```

<210> SEQ ID NO 12
<211> LENGTH: 476
<212> TYPE: PRT
<213> ORGANISM: Arthrobacter citreus
<220> FEATURE:
<223> OTHER INFORMATION: mutant transaminase CNB03-03

<400> SEQUENCE: 12

```
Met Gly Leu Thr Val Gln Lys Ile Asn Trp Glu Gln Val Lys Glu Trp
 1               5                  10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Thr Pro Gly
        35                  40                  45

Gly Thr Arg Leu Leu Asp Phe Phe Asn Gln Leu Cys Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Tyr Ser Ser Ala Val Leu Met Ala
            180                 185                 190

Pro Ser Ser Asn Thr Phe Gln Asp Ser Asn Gly Asn Cys Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Val Pro Gln Ile Arg
```

-continued

```
                245                 250                 255

Lys Met Thr Lys Glu Leu Gly Val Leu Trp Ile Ser Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475
```

<210> SEQ ID NO 13
<211> LENGTH: 1431
<212> TYPE: DNA
<213> ORGANISM: Arthrobacter citreus
<220> FEATURE:
<223> OTHER INFORMATION: mutant transaminase CNB04-01

<400> SEQUENCE: 13

```
atgggtttaa cagtgcaaaa aataaactgg gagcaagtta aagaatggga tcgtaaatac      60

ctgatgagga cgtttagtac ccagaacgag tatcaacctg taccgattga atcaacagaa     120

ggtgactatt tgattacgcc tggtggcaca agattattag atttcttcaa tcaactttgt     180

tgtgtcaatt taggccagaa aaatcaaaaa gttaatgctg caatcaagga ggctttagac     240

cgatatggtt ttgtatggga tacttatgca actgattata aagccaaagc agccaagata     300

attattgagg atattttagg tgatgaagac tggccaggaa aggttaggtt cgtatcaaca     360

ggaagtgaag cagtggaaac ggcactgaat atcgcgaggt tatatacaaa tcgcccacta     420

gtggttacac gagaacacga ttatcatggt tggactggtg gagctgctac tgttactcga     480

ttaaggtcat ttcgaagtgg tttagttggg gaaaattcag aatctttttc agcacaaata     540

cctggctcat catatagtag tgctgttttg atggcgccat cctctaacac gtttcaggat     600

tcgaacggca actacctaaa agatgaaaac ggggaattgt tgagtgtaaa gtatacacgt     660

cgtatgatag aaaactatgg tccggaacaa gtggcagcag tgataactga agtatcgcaa     720

ggtgtaggct ctactatgcc cccatatgaa tacgttccac aaatccgaaa aatgacaaaa     780
```

-continued gaactaggtg tcctttggat tagtgatgaa gttcttactg gctttgggcg tacagggaag 840
tggtttggat atcagcatta tggggtacag ccagatataa tcactatggg taaaggactc 900
tccagttcct cactccctgc tggcgctgtc gtagttagta aggaaattgc agcgtttatg 960
gataagcacc gatgggagtc agtatccacc tatgctggtc atccagttgc gatggctgcg 1020
gtttgtgcaa atttagaagt aatgatggaa gaaaaccttg ttgagcaagc gaagaacagc 1080
ggcgagtata taaggagtaa acttgaactt ctgcaagaaa agcataaaag tataggcaat 1140
ttcgacggat atggcctttt atggatagtt gatattgtga atgccaagac taagactcct 1200
tacgtaaaat tggacaggaa ctttaggcac gggatgaatc caaatcaaat cccgacacaa 1260
atcattatgg aaaaagcgct agaaaaagga gtgctgattg gtggagcaat gcctaataca 1320
atgagaattg gtgcatcttt gaatgttagt cgcggagaca tcgataaagc aatggatgca 1380
ctggattatg cacttgacta tctagaaagt ggagaatggc agcaatccta a 1431

<210> SEQ ID NO 14
<211> LENGTH: 476
<212> TYPE: PRT
<213> ORGANISM: Arthrobacter citreus
<220> FEATURE:
<223> OTHER INFORMATION: mutant transaminase CNB04-01

<400> SEQUENCE: 14

Met Gly Leu Thr Val Gln Lys Ile Asn Trp Glu Gln Val Lys Glu Trp
1 5 10 15

Asp Arg Lys Tyr Leu Met Arg Thr Phe Ser Thr Gln Asn Glu Tyr Gln
20 25 30

Pro Val Pro Ile Glu Ser Thr Glu Gly Asp Tyr Leu Ile Thr Pro Gly
35 40 45

Gly Thr Arg Leu Leu Asp Phe Phe Asn Gln Leu Cys Cys Val Asn Leu
50 55 60

Gly Gln Lys Asn Gln Lys Val Asn Ala Ala Ile Lys Glu Ala Leu Asp
65 70 75 80

Arg Tyr Gly Phe Val Trp Asp Thr Tyr Ala Thr Asp Tyr Lys Ala Lys
85 90 95

Ala Ala Lys Ile Ile Ile Glu Asp Ile Leu Gly Asp Glu Asp Trp Pro
100 105 110

Gly Lys Val Arg Phe Val Ser Thr Gly Ser Glu Ala Val Glu Thr Ala
115 120 125

Leu Asn Ile Ala Arg Leu Tyr Thr Asn Arg Pro Leu Val Val Thr Arg
130 135 140

Glu His Asp Tyr His Gly Trp Thr Gly Gly Ala Ala Thr Val Thr Arg
145 150 155 160

Leu Arg Ser Phe Arg Ser Gly Leu Val Gly Glu Asn Ser Glu Ser Phe
165 170 175

Ser Ala Gln Ile Pro Gly Ser Ser Tyr Ser Ser Ala Val Leu Met Ala
180 185 190

Pro Ser Ser Asn Thr Phe Gln Asp Ser Asn Gly Asn Tyr Leu Lys Asp
195 200 205

Glu Asn Gly Glu Leu Leu Ser Val Lys Tyr Thr Arg Arg Met Ile Glu
210 215 220

Asn Tyr Gly Pro Glu Gln Val Ala Ala Val Ile Thr Glu Val Ser Gln
225 230 235 240

Gly Val Gly Ser Thr Met Pro Pro Tyr Glu Tyr Val Pro Gln Ile Arg

-continued

```
            245                 250                 255

Lys Met Thr Lys Glu Leu Gly Val Leu Trp Ile Ser Asp Glu Val Leu
        260                 265                 270

Thr Gly Phe Gly Arg Thr Gly Lys Trp Phe Gly Tyr Gln His Tyr Gly
    275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
            325                 330                 335

Ala Met Ala Ala Val Cys Ala Asn Leu Glu Val Met Met Glu Glu Asn
        340                 345                 350

Leu Val Glu Gln Ala Lys Asn Ser Gly Glu Tyr Ile Arg Ser Lys Leu
    355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
            405                 410                 415

Ile Pro Thr Gln Ile Ile Met Glu Lys Ala Leu Glu Lys Gly Val Leu
        420                 425                 430

Ile Gly Gly Ala Met Pro Asn Thr Met Arg Ile Gly Ala Ser Leu Asn
    435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475
```

```
<210> SEQ ID NO 15
<211> LENGTH: 1431
<212> TYPE: DNA
<213> ORGANISM: Arthrobacter citreus
<220> FEATURE:
<223> OTHER INFORMATION: mutant transaminase CNB05-01

<400> SEQUENCE: 15

atgggtttaa cagtgcaaaa aataaactgg gagcaagtta aagaatggga tcgtaaatac      60

ctgatgagga cgtttagtac ccagaacgag tatcaacctg taccgattga atcaacagaa     120

ggtgactatt tgattacacc tggtggcaca agattattag atttcttcaa tcaactttgt     180

tgtgtcaatt taggccagaa aaatcaaaaa gttaatgctg caatcaagga ggctttagac     240

cgatatggtt ttgtatggga tacttatgca actgattata aagccaaagc agccaagata     300

attattgagg atattttagg tgatgaagac tggccaggaa aggttaggtt cgtatcaaca     360

ggaagtgaag cagtggaaac ggcactgaat atcgcgaggt tatatacaaa tcgcccacta     420

gtggttacac gagaacacga ttatcatggt tggactggtg gagctgctac tgttactcga     480

ttaaggtcat ttcgaagtgg tttagttggg gaaaattcag aatctttttc agcacaaata     540

cctggctcat catgtagtag tgctgttttg atggcgccat cctctaacac gtttcaggat     600

tcgaacggca actacctaaa agatgaaaac ggggaattgt tgagtgtaaa gtatacacgt     660

cgtatgatag aaaactatgg tccggaacaa gtggcagcag tgataactga agtatcgcaa     720

ggtgtaggct ctactatgcc cccatatgaa tacgttccac aaatccgaaa aatgacaaaa     780
```

-continued

```
gaactaggtg tcctttggat tagtgatgaa gttcttactg gctttgggcg tacagggaag    840

tggtttggat atcagcatta tggggtacag ccagatataa tcactatggg taaaggactc    900

tccagttcct cactccctgc tggcgctgtc gtagttagta aggaaattgc agcgtttatg    960

gataagcacc gatgggagtc agtatccacc tatgctggtc atccagttgc gatggctgcg   1020

gtttgtgcaa atttagaagt aatgatggaa gaaaaccttg ttgagcaagc gaagaacagc   1080

ggcgagtata taaggagtaa acttgaactt ctgcaagaaa agcataaaag tataggcaat   1140

ttcgacggat atggcctttt atggatagtt gatattgtga atgccaagac taagactcct   1200

tacgtaaaat tggacaggaa ctttaggcac gggatgaatc caaatcaaat cccgacacaa   1260

atcattatgg aaaaagcgct agaaaaagga gtgctgattg gtggagcaat gcctaataca   1320

atgagaattg gtgcatcttt gaatgttagt cgcggagaca tcgataaagc aatggatgca   1380

ctggattatg cacttgacta tctagaaagt ggagaatggc agcaatccta a            1431
```

```
<210> SEQ ID NO 16
<211> LENGTH: 476
<212> TYPE: PRT
<213> ORGANISM: Arthrobacter citreus
<220> FEATURE:
<223> OTHER INFORMATION: mutant transaminase CNB05-01

<400> SEQUENCE: 16

Met Gly Leu Thr Val Gln Lys Ile Asn Trp Glu Gln Val Lys Glu Trp
 1               5                  10                  15

Asp Arg Lys Tyr Leu Met Arg Thr Phe Ser Thr Gln Asn Glu Tyr Gln
            20                  25                  30

Pro Val Pro Ile Glu Ser Thr Glu Gly Asp Tyr Leu Ile Thr Pro Gly
        35                  40                  45

Gly Thr Arg Leu Leu Asp Phe Phe Asn Gln Leu Cys Cys Val Asn Leu
    50                  55                  60

Gly Gln Lys Asn Gln Lys Val Asn Ala Ala Ile Lys Glu Ala Leu Asp
65                  70                  75                  80

Arg Tyr Gly Phe Val Trp Asp Thr Tyr Ala Thr Asp Tyr Lys Ala Lys
                85                  90                  95

Ala Ala Lys Ile Ile Ile Glu Asp Ile Leu Gly Asp Glu Asp Trp Pro
            100                 105                 110

Gly Lys Val Arg Phe Val Ser Thr Gly Ser Glu Ala Val Glu Thr Ala
        115                 120                 125

Leu Asn Ile Ala Arg Leu Tyr Thr Asn Arg Pro Leu Val Val Thr Arg
    130                 135                 140

Glu His Asp Tyr His Gly Trp Thr Gly Gly Ala Ala Thr Val Thr Arg
145                 150                 155                 160

Leu Arg Ser Phe Arg Ser Gly Leu Val Gly Glu Asn Ser Glu Ser Phe
                165                 170                 175

Ser Ala Gln Ile Pro Gly Ser Ser Cys Ser Ser Ala Val Leu Met Ala
            180                 185                 190

Pro Ser Ser Asn Thr Phe Gln Asp Ser Asn Gly Asn Tyr Leu Lys Asp
        195                 200                 205

Glu Asn Gly Glu Leu Leu Ser Val Lys Tyr Thr Arg Arg Met Ile Glu
    210                 215                 220

Asn Tyr Gly Pro Glu Gln Val Ala Ala Val Ile Thr Glu Val Ser Gln
225                 230                 235                 240

Gly Val Gly Ser Thr Met Pro Pro Tyr Glu Tyr Val Pro Gln Ile Arg
```

-continued

```
                245                 250                 255

Lys Met Thr Lys Glu Leu Gly Val Leu Trp Ile Ser Asp Glu Val Leu
            260                 265                 270

Thr Gly Phe Gly Arg Thr Gly Lys Trp Phe Gly Tyr Gln His Tyr Gly
        275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys His Arg Trp Glu Ser Val Ser Thr Tyr Ala Gly His Pro Val
                325                 330                 335

Ala Met Ala Ala Val Cys Ala Asn Leu Glu Val Met Met Glu Glu Asn
            340                 345                 350

Leu Val Glu Gln Ala Lys Asn Ser Gly Glu Tyr Ile Arg Ser Lys Leu
        355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
                405                 410                 415

Ile Pro Thr Gln Ile Ile Met Glu Lys Ala Leu Glu Lys Gly Val Leu
            420                 425                 430

Ile Gly Gly Ala Met Pro Asn Thr Met Arg Ile Gly Ala Ser Leu Asn
        435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475
```

<210> SEQ ID NO 17
<211> LENGTH: 1431
<212> TYPE: DNA
<213> ORGANISM: Arthrobacter citreus
<220> FEATURE:
<223> OTHER INFORMATION: mutant transaminase CNB05-02

<400> SEQUENCE: 17

```
atgggtttaa cagtgcaaaa aataaactgg gagcaagtta aagaatggga tcgtaaatac     60

ctgatgagga cgtttagtac ccagaacgag tatcaacctg taccgattga atcaacagaa    120

ggtgactatt tgattacacc tggtggcaca agattattag atttcttcaa tcaactttgt    180

tgtgtcaatt taggccagaa aaatcaaaaa gttaatgctg caatcaagga ggctttagac    240

cgatatggtt ttgtatggga tacttatgca actgattata aagccaaagc agccaagata    300

attattgagg atattttagg tgatgaagac tggccaggaa aggttaggtt cgtatcaaca    360

ggaagtgaag cagtggaaac ggcactgaat atcgcgaggt tatatacaaa tcgcccacta    420

gtggttacac gagaacacga ttatcatggt tggactggtg gagctgctac tgttactcga    480

ttaaggtcat ttcgaagtgg tttagttggg gaaaattcag aatctttttc agcacaaata    540

cctggctcat catgtagtag tgctgttttg atggcgccat cctctaacac gtttcaggat    600

tcgaacggca actgcctaaa agatgaaaac ggggaattgt tgagtgtaaa gtatacacgt    660

cgtatgatag aaaactatgg tccggaacaa gtggcagcag tgataactga agtatcgcaa    720

ggtgtaggct ctactatgcc cccatatgaa tacattccac aaatccgaaa aatgacaaaa    780
```

-continued gaactaggtg tcctttggat tagtgatgaa gttcttactg gctttgggcg tacagggaag 840
tggtttggat atcagcatta tggggtacag ccagatataa tcactatggg taaaggactc 900
tccagttcct cactccctgc tggcgctgtc gtagttagta aggaaattgc agcgtttatg 960
gataagtacc gatgggagtc agtatccacc tatgctggtc atccagttgc gatggctgcg 1020
gtttgtgcaa atttagaagt aatgatggaa gaaaaccttg ttgagcaagc gaagaacagc 1080
ggcgagtata taaggagtaa acttgaactt ctgcaagaaa agcataaaag tataggcaat 1140
ttcgacggat atggcctttt atggatagtt gatattgtga atgccaagac taagactcct 1200
tacgtaaaat tggacaggaa ctttaggcac gggatgaatc caaatcaaat cccgacacaa 1260
atcattatgg aaaaagcgct agaaaaagga gtgctgattg gtggagcaat gcctaataca 1320
atgagaattg gtgcatcttt gaatgttagt cgcggagaca tcgataaagc aatggatgca 1380
ctggattatg cacttgacta tctagaaagt ggagaatggc agcaatccta a 1431

<210> SEQ ID NO 18
<211> LENGTH: 476
<212> TYPE: PRT
<213> ORGANISM: Arthrobacter citreus
<220> FEATURE:
<223> OTHER INFORMATION: mutant transaminase CNB05-02

<400> SEQUENCE: 18

Met Gly Leu Thr Val Gln Lys Ile Asn Trp Glu Gln Val Lys Glu Trp
1 5 10 15

Asp Arg Lys Tyr Leu Met Arg Thr Phe Ser Thr Gln Asn Glu Tyr Gln
20 25 30

Pro Val Pro Ile Glu Ser Thr Glu Gly Asp Tyr Leu Ile Thr Pro Gly
35 40 45

Gly Thr Arg Leu Leu Asp Phe Phe Asn Gln Leu Cys Cys Val Asn Leu
50 55 60

Gly Gln Lys Asn Gln Lys Val Asn Ala Ala Ile Lys Glu Ala Leu Asp
65 70 75 80

Arg Tyr Gly Phe Val Trp Asp Thr Tyr Ala Thr Asp Tyr Lys Ala Lys
85 90 95

Ala Ala Lys Ile Ile Ile Glu Asp Ile Leu Gly Asp Glu Asp Trp Pro
100 105 110

Gly Lys Val Arg Phe Val Ser Thr Gly Ser Glu Ala Val Glu Thr Ala
115 120 125

Leu Asn Ile Ala Arg Leu Tyr Thr Asn Arg Pro Leu Val Val Thr Arg
130 135 140

Glu His Asp Tyr His Gly Trp Thr Gly Gly Ala Ala Thr Val Thr Arg
145 150 155 160

Leu Arg Ser Phe Arg Ser Gly Leu Val Gly Glu Asn Ser Glu Ser Phe
165 170 175

Ser Ala Gln Ile Pro Gly Ser Ser Cys Ser Ser Ala Val Leu Met Ala
180 185 190

Pro Ser Ser Asn Thr Phe Gln Asp Ser Asn Gly Asn Cys Leu Lys Asp
195 200 205

Glu Asn Gly Glu Leu Leu Ser Val Lys Tyr Thr Arg Arg Met Ile Glu
210 215 220

Asn Tyr Gly Pro Glu Gln Val Ala Ala Val Ile Thr Glu Val Ser Gln
225 230 235 240

Gly Val Gly Ser Thr Met Pro Pro Tyr Glu Tyr Ile Pro Gln Ile Arg

-continued

```
            245                 250                 255

Lys Met Thr Lys Glu Leu Gly Val Leu Trp Ile Ser Asp Glu Val Leu
        260                 265                 270

Thr Gly Phe Gly Arg Thr Gly Lys Trp Phe Gly Tyr Gln His Tyr Gly
    275                 280                 285

Val Gln Pro Asp Ile Ile Thr Met Gly Lys Gly Leu Ser Ser Ser Ser
    290                 295                 300

Leu Pro Ala Gly Ala Val Val Val Ser Lys Glu Ile Ala Ala Phe Met
305                 310                 315                 320

Asp Lys Tyr Arg Trp Glu Ser Val Ser Thr Tyr Ala Gly His Pro Val
            325                 330                 335

Ala Met Ala Ala Val Cys Ala Asn Leu Glu Val Met Met Glu Glu Asn
        340                 345                 350

Leu Val Glu Gln Ala Lys Asn Ser Gly Glu Tyr Ile Arg Ser Lys Leu
    355                 360                 365

Glu Leu Leu Gln Glu Lys His Lys Ser Ile Gly Asn Phe Asp Gly Tyr
    370                 375                 380

Gly Leu Leu Trp Ile Val Asp Ile Val Asn Ala Lys Thr Lys Thr Pro
385                 390                 395                 400

Tyr Val Lys Leu Asp Arg Asn Phe Arg His Gly Met Asn Pro Asn Gln
            405                 410                 415

Ile Pro Thr Gln Ile Ile Met Glu Lys Ala Leu Glu Lys Gly Val Leu
        420                 425                 430

Ile Gly Gly Ala Met Pro Asn Thr Met Arg Ile Gly Ala Ser Leu Asn
    435                 440                 445

Val Ser Arg Gly Asp Ile Asp Lys Ala Met Asp Ala Leu Asp Tyr Ala
    450                 455                 460

Leu Asp Tyr Leu Glu Ser Gly Glu Trp Gln Gln Ser
465                 470                 475
```

THERMOSTABLE OMEGA-TRANSAMINASES

This application is a division of Ser. No. 11/295,696 filed Dec. 7, 2005, now matured into U.S. Pat. No. 7,172,885 which claims priority to provisional application Ser. No. 60/634,526 filed Dec. 10, 2004. Each of these applications is incorporated by reference in its entirety herein.

FIELD OF THE INVENTION

The invention relates to omega-transaminases and their use in enantiomeric enrichment and stereoselective synthesis.

BACKGROUND OF THE INVENTION

Chiral molecules, such as single-enantiomer drugs, can be produced by biotransformation, asymmetric synthesis using chiral catalysts or reagents, resolution or separation techniques, and the like. There is a continuing need in the art for improved and efficient methods of preparing chiral molecules.

BRIEF DESCRIPTION OF THE FIGURES

FIG. 3A, values of initial rates. FIG. 3B, rates over time.

DETAILED DESCRIPTION OF THE INVENTION

Figure 1:
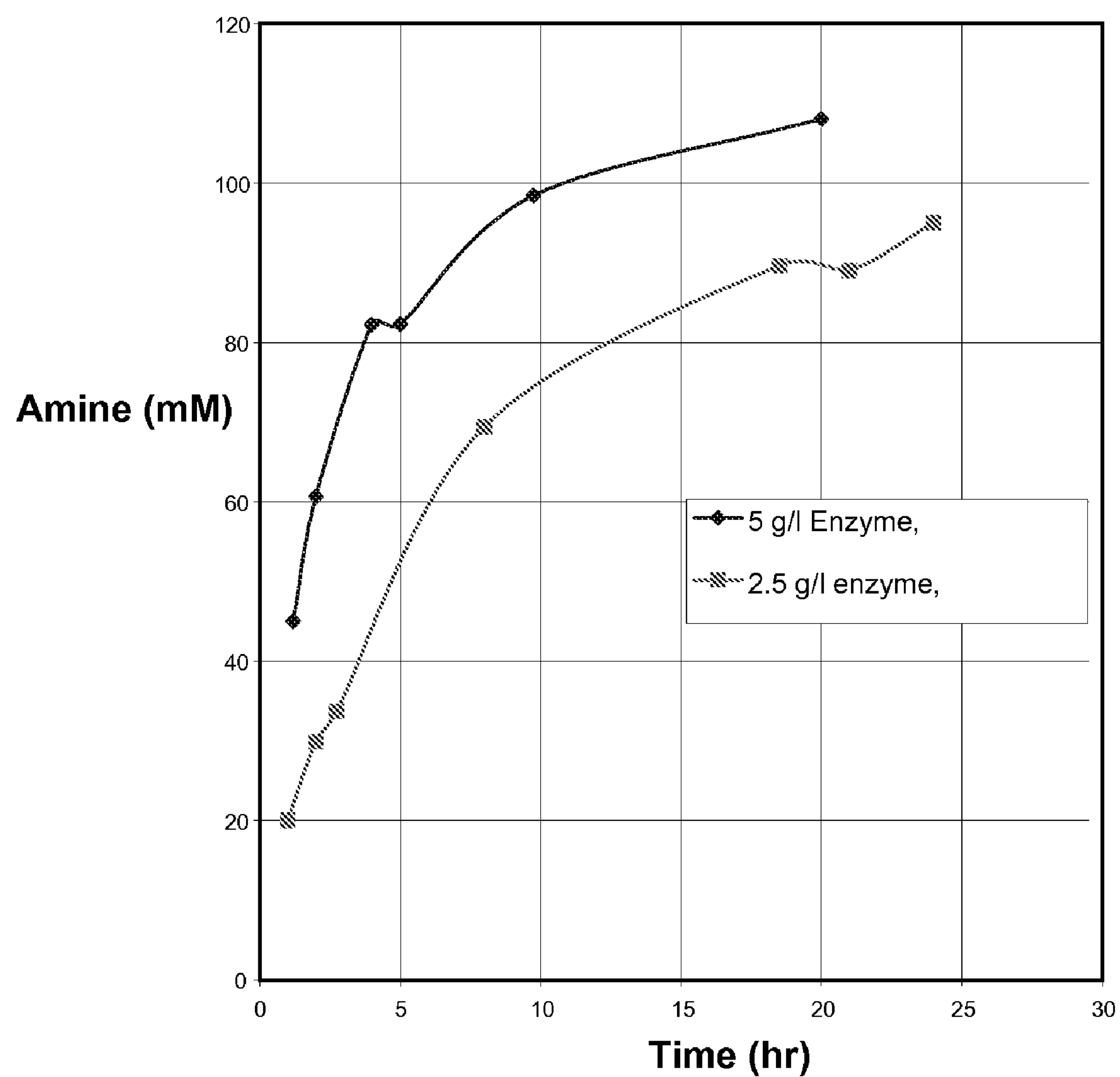
FIG. 1. Typical reaction curves to follow the formation of product amine using of 5 g/L and 2.5 g/L of the enzyme CNB03-03 (SEQ ID NO:12) for stereoselective synthesis at 58-60° C.

Transaminases, also called aminotransaminases, catalyze the transfer of an amino group from a donor amine to an amine acceptor molecule. Omega-transaminases (ω-transaminases) transfer amine groups which are separated from a carboxyl group by at least one methylene insertion. The invention provides thermostable omega-transaminases, particularly thermostable omega-transaminases which have a high reaction rate and which are tolerant to high concentrations of donor amine. Thermostable omega-transaminases of the invention can be used to enrich enantiomerically a mixture of chiral amines or to synthesize stereoselectively one of a pair of chiral amines in which the amino group is bound to a non-terminal, chirally substituted, carbon atom. Methods of the invention provide cost-effective and specific means for producing chiral molecules.

Thermostable Omega-Transaminases

The amino acid sequence of a wild-type omega-transaminase from *Arthrobacter* citreus is shown in SEQ ID NO:2. Thermostable omega transaminases of the invention comprise an amino acid sequence which differs from the amino acid sequence shown in SEQ ID NO:2 at each of positions 242, 245, 255, and 268 with one or more additional amino acid substitutions at positions 46, 48, 60, 164, 185, 186, 195, 197, 205, 252, 323, 409, 424, and 436.

For example, some thermostable transaminases have an additional amino acid substitution at position 46 (e.g., SEQ ID NOS:12, 14, 16, and 18) or at position 185 (e.g., SEQ ID NOS:16 and 18). Others have additional amino acid substitutions at positions 48, 195, and 197 (e.g., SEQ ID NOS:8, 10, 12, 14, 16, and 18); positions 46, 48, 195, and 197 (e.g., SEQ ID NOS:16 and 18); positions 60, 164, 186, 252, 409, and 426 (e.g., SEQ ID NOS:6, 8, 10, 12, 16, and 18); positions 48, 60, 164, 186, 195, 197, 252, 409, and 436 (e.g., SEQ ID NOS:8 and 12); positions 48, 60, 164, 186, 195, 197, 252, 409, 424, and 436 (SEQ ID NOS:8, 10, and 12); or positions 46, 48, 60, 164, 185, 186, 195, 197, 409, 424, and 436 (e.g., SEQ ID NOS:16 and 18).

Certain thermostable omega transaminases of the invention comprise an amino acid sequence which differs from the amino acid sequence shown in SEQ ID NO:2 at each of positions 60, 164, 186, 242, 245, 252, 255, 268, 409, and 436; in these transaminases, one or more substitutions also can be made at positions 46, 48, 195, 197, and 424.

Other thermostable omega transaminases of the invention comprise an amino acid sequence which differs from the amino acid sequence shown in SEQ ID NO:2 at each of positions 46, 48, 195, 197, 242, 245, and 255; in these transaminases, one or more substitutions also can be made at postitions 60, 164, 185, 186, 205, 252, 323, 409, 424, and 436.

Preferred substitutions are provided in Table 1 and include all possible combinations of the possible substitutions shown. The most preferred substitutions are indicated in bold and underlined.

TABLE 1

Preferred amino acid substitutions with respect to SEQ ID NO:2.

| amino acid position no. | wild-type | thermostable omega-transaminase |
|---|---|---|
| 46 | Met | Gly, Ser, **Thr**, Cys, Tyr, Asp, Glu, Ala, Val, Leu, Ile, Pro, Phe, and Trp |
| 48 | Asp | **Gly**, Ser, Thr, Cys, Tyr, and Glu |
| 60 | Tyr | Gly, Ser, Thr, **Cys**, Asp, and Glu |
| 164 | Tyr | Ala, Val, Leu, Ile, Pro, **Phe**, Trp, and Met |
| 185 | Tyr | Gly, Ser, Thr, **Cys**, Asp, and Glu |
| 186 | Asp | Gly, **Ser**, Thr, Cys, Tyr, and Glu |
| 195 | Pro | Gly, **Ser**, Thr, Cys, Tyr, Asp, Glu, Ala, Val, Leu, Ile, Phe, Trp, and Met |
| 197 | Met | Gly, Ser, **Thr**, Cys, Tyr, Asp, Glu, Ala, Val, Leu, Ile, Pro, Phe, and Trp |
| 205 | Cys | **Tyr**, Gly, Ser, Thr, Asp, and Glu |
| 242 | Ala | **Val**, Leu, Ile, Pro, Phe, Trp, and Met |
| 245 | Ala | Gly, Ser, **Thr**, Cys, Tyr, Asp, and Glu |
| 252 | Ile | Ala, **Val**, Leu, Pro, Phe, Trp, and Met |
| 255 | Phe | Ala, Val, Leu, **Ile**, Pro, Trp, and Met |
| 268 | Asp | Gly, **Ser**, Thr, Cys, Tyr, and Glu |
| 323 | His | **Tyr**, Gly, Ser, Thr, Cys, Asp, and Glu |
| 409 | Thr | Lys, **Arg**, and His |
| 424 | Lys | **Glu**, Asp, Arg, and His |
| 436 | Val | **Ala**, Leu, Ile, Pro, Phe, Trp, and Met |

Omega-transaminases with the substitutions described in Table 1 are thermostable. "Thermostable" means that the enzyme is active (able to carry out the reaction, either stereoselective synthesis or enantiomeric enrichment, as indicated by the continued formation of product) and stable (active for at least 10 hours) up to at least 40° C., preferably up to at least 50-60° C. (e.g., at least 50, 51, 52, 53, 54, 55, 56, 57, 58, 59, or 60° C.), even more preferably up to at least 55-63° C. (e.g., at least 55, 56, 57, 58, 59, 60, 61, 62, or 63° C.). Activity is measured by the monitoring the formation of product as a function of time in a reaction. Typical stereoselective synthesis and enantiomeric enrichment reactions are described in Example 1.

Such thermostable omega-transaminases also have a greater tolerance to high donor amine concentrations than the wild-type enzyme (i.e., they are active and stable) in the presence of high concentration of amine. Preferred thermostable omega-transaminases are active and stable for at least 10 hours in the presence of >500 mM amine. Omega-transaminases with optional additional substitutions at positions 46, 48, 195, 197, and 424 also have higher reaction rates than the wild-type enzyme. These higher reaction rates typically are 1.2 to 3 times higher than the reaction rate of the wild-type enzyme as measured by the rate of formation of product (see Example 1).

The amino acid sequences of several thermostable omega-transaminases are shown in SEQ ID NOS:6 ("Chir9867"), 8 ("CNB03-01"), 10 ("CNB03-02"), 12 ("CNB03-03"), 14 ("CNB04-01"), 16 ("CNB05-01"), and 18 ("CNB05-02") and in Table 2, below. In Table 2, amino acid substitutions with respect to the wild-type sequence are shown in bold. Thermostable omega-transaminases of the invention do not have the amino acid sequence shown in SEQ ID NO:4 and encoded by the nucleotide sequence shown in SEQ ID NO:3; SEQ ID NO:4 is the amino acid sequence of an omega-transaminase which is tolerant to high donor amine concentrations but which is not thermostable.

TABLE 2

Amino acid substitutions in thermostable omega-transaminases.

| amino acid position | wild-type (SEQ ID NO:2) | Chir9867 (SEQ ID NO:6) | CNB03-01 (SEQ ID NO:8) | CNB03-02 (SEQ ID NO:10) | CNB03-03 (SEQ ID NO:12) | CNB04-01 (SEQ ID NO:14) | CNB05-01 (SEQ ID NO:16) | CNB05-02 (SEQ ID NO:18) |
|---|---|---|---|---|---|---|---|---|
| 46 | Met | Met | Met | Met | **Thr** | **Thr** | **Thr** | **Thr** |
| 48 | Asp | Asp | **Gly** | **Gly** | **Gly** | **Gly** | **Gly** | **Gly** |
| 60 | Tyr | **Cys** | **Cys** | **Cys** | **Cys** | Tyr | **Cys** | **Cys** |
| 164 | Tyr | **Phe** | **Phe** | **Phe** | **Phe** | Tyr | **Phe** | **Phe** |
| 185 | Tyr | Tyr | Tyr | Tyr | Tyr | Tyr | **Cys** | **Cys** |
| 186 | Asp | **Ser** | **Ser** | **Ser** | **Ser** | Asp | **Ser** | **Ser** |
| 195 | Pro | Pro | **Ser** | **Ser** | **Ser** | **Ser** | **Ser** | **Ser** |
| 197 | Met | Met | **Thr** | **Thr** | **Thr** | **Thr** | **Thr** | **Thr** |
| 205 | Cys | Cys | Cys | Cys | Cys | Cys | **Tyr** | Cys |
| 242 | Ala | **Val** | **Val** | **Val** | **Val** | **Val** | **Val** | **Val** |
| 245 | Ala | **Thr** | **Thr** | **Thr** | **Thr** | **Thr** | **Thr** | **Thr** |
| 252 | Ile | **Val** | **Val** | **Val** | **Val** | **Val** | **Val** | Ile |
| 255 | Phe | **Ile** | **Ile** | **Ile** | **Ile** | **Ile** | **Ile** | **Ile** |
| 268 | Asp | **Ser** | **Ser** | **Ser** | **Ser** | **Ser** | **Ser** | **Ser** |
| 323 | His | His | His | His | His | His | His | **Tyr** |
| 409 | Thr | **Arg** | **Arg** | **Arg** | **Arg** | Thr | **Arg** | **Arg** |
| 424 | Lys | **Glu** | **Glu** | Lys | **Glu** | Lys | **Glu** | **Glu** |
| 436 | Val | **Ala** | **Ala** | **Ala** | **Ala** | Val | **Ala** | **Ala** |

Preparation of Thermostable Omega-Transaminases

Thermostable omega-transaminases of the invention can be produced by any suitable means known in the art (e.g., recombinantly, for example in a host cell, or by chemical synthesis). Preferably the enzymes are produced using high cell density fermentation with recombinant *E. coli*.

Recombinant Production of Thermostable Omega-Transaminases Nucleic Acid Molecules The sequence listing provides coding sequences for preferred thermostable omega-transaminases of the invention (SEQ ID NOS:5, 7, 9, 11, 13, 15, and 17 encode SEQ ID NOS:6, 8, 10, 12, 14, 16, and 18, respectively). Any nucleotide sequence which encodes a particular thermostable omega-transaminase, however, can be used to produce that enzyme recombinantly. For example, sequences encoding a thermostable omega-transaminase can be synthesized, in whole or in part, using chemical methods well known in the art (see Caruthers et al., *Nucl. Acids Res. Symp. Ser.* 215-223, 1980; Horn et al. *Nucl. Acids Res. Symp. Ser.* 225-232, 1980). Alternatively, nucleic acid molecules encoding the wild-type omega-transaminase of SEQ ID NO:2 (e.g., SEQ ID NO:1) can be modified to encode a thermostable omega-transaminase of the invention. If desired, such molecules can be isolated from *Arthrobacter citreus* bacteria using standard nucleic acid purification techniques or can be synthesized using an amplification technique, such as the polymerase chain reaction (PCR), or by using an automatic synthesizer. Methods for isolating nucleic acids are routine and are known in the art. Any such technique for obtaining a nucleic acid molecules can be used to obtain a nucleic acid molecule which encodes the wild-type omega-transaminase.

cDNA molecules encoding thermostable omega-transaminases of the invention can be made with standard molecular biology techniques, using mRNA as a template. cDNA molecules can thereafter be replicated using molecular biology techniques well known in the art. An amplification technique, such as PCR, can be used to obtain additional copies of polynucleotides of the invention.

If desired, the nucleotide sequences disclosed herein can be engineered using methods generally known in the art to alter coding sequences for thermostable omega-transaminases of the invention for a variety of reasons, including but not limited to, alterations which modify the cloning, processing, and/or expression of the polypeptide or mRNA product. Sequence modifications, such as the addition of a purification tag sequence or codon optimization, can be used to facilitate expression. These methods are well known in the art and are further described, for example, in PCT/US04/024868.

Expression Vectors

A nucleic acid molecule which encodes a thermostable omega-transaminase of the invention can be inserted into an expression vector which contains the necessary elements for the transcription and translation of the inserted coding sequence. Methods which are well known to those skilled in the art can be used to construct expression vectors containing sequences encoding enzymes of the invention and appropriate transcriptional and translational control elements. These methods include in vitro recombinant DNA techniques as well as synthetic techniques.

Host Cells

A host cell can be prokaryotic or eukaryotic. Useful host cells include *Arthrobacter* citreus itself, *E. coli, Bacillus subtilis, Vibrio cholerae, Salmonella typhi, Salmonella typhimurium, Neisseria lactamica, Neisseria cinerea, Mycobacteria* (e.g., *M. tuberculosis*), yeasts, etc. Many types of host cells are available, for example, from the American Type Culture Collection (ATCC; 10801 University Boulevard, Manassas, Va. 20110-2209) and can be chosen to ensure the correct modification and processing of a foreign protein. See, e.g., WO 01/98340.

Expression constructs can be introduced into host cells using well-established techniques. Such techniques include, but are not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Host cells transformed with expression vectors can be cultured under conditions suitable for the expression and recovery of the enzyme from the cell culture. The enzyme produced by a transformed cell can be secreted or contained intracellularly depending on the nucleotide sequence and/or the expression vector used.

Purification of Thermostable Omega-Transaminases

A recombinantly produced thermostable omega-transaminase can be isolated from a host cell engineered to produce the enzyme. A purified thermostable omega-transaminase is separated from other components in the cell, such as proteins, carbohydrates, or lipids, using methods well-known in the art. Such methods include, but are not limited to, size exclusion chromatography, ammonium sulfate fractionation, ion exchange chromatography, affinity chromatography, and preparative gel electrophoresis. A preparation of purified thermostable omega-transaminase is at least 80% pure; preferably, the preparations are 90%, 95%, or 99% pure. Purity of the preparations can be assessed by any means known in the art, such as SDS-polyacrylamide gel electrophoresis.

Chemical Synthesis of Thermostable Omega-Transaminases

Thermostable omega-transaminases of the invention can be synthesized, for example, using solid-phase techniques. See, e.g., Merrifield, *J. Am. Chem. Soc.* 85, 2149-54, 1963; Roberge et al., *Science* 269, 202-04, 1995. Protein synthesis can be performed using manual techniques or by automation. Automated synthesis can be achieved, for example, using Applied Biosystems 431A Peptide Synthesizer (Perkin Elmer). Optionally, fragments of a thermostable omega-transferase can be synthesized separately and combined using chemical methods to produce a full-length molecule.

Methods of Preparing Chiral Molecules

The invention provides methods of using thermostable omega-transaminases to prepare chiral molecules, either by enantiomerically enriching a mixture of chiral amines or by stereoselectively synthesizing one of a pair of chiral amines.

The enzymatic equilibrium reaction in which omega-transaminases participate is illustrated below:

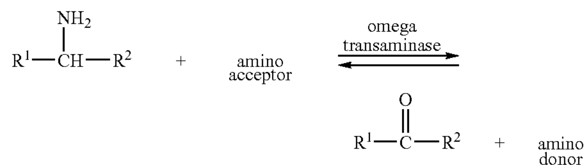

in which each of $R^1$ and $R^2$, when taken independently, is an alkyl or aryl group which is unsubstituted or substituted with one or more enzymatically non-inhibiting groups and $R^1$ is different from $R^2$ in structure or chirality, or $R^1$ and $R^2$, taken together, are a hydrocarbon chain of 4 or more carbon atoms containing a center of chirality.

Amino Acceptors

An "amino acceptor" is a carbonyl compound which accepts an amino group from a donor amine. Amino acceptors include ketocarboxylic acids and alkanones. Typical ketocarboxylic acids are α-keto carboxylic acids such as glyoxalic acid, pyruvic acid, oxaloacetic acid, and the like, as well as salts of these acids. Amino acceptors also include or substances which are converted to an amino acceptor by other enzymes or whole cell processes, such as fumaric acid (which can be converted to oxaloacetic acid), glucose (which can be converted to pyruvate), lactate, maleic acid, etc.

Amino Donors

An "amino donor" is an amino compound which donates an amino group to the amino acceptor, thereby becoming a carbonyl species. Typical amino donors include the non-chiral amino acid glycine and chiral amino acids having the S-configuration such as L-alanine or L-aspartic acid; amino donors, however, need not be amino acids. For example, amines such as S-2-aminobutane, propyl amine, benzyl amine, etc. also can be used as amino donors.

Chiral Amines

Chiral amines have the formula:

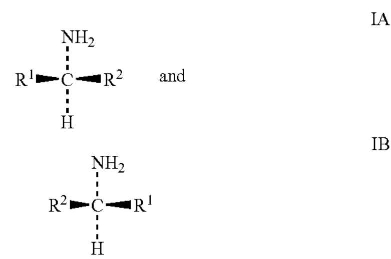

in which each of $R^1$ and $R^2$ are as defined above. The compounds of Formulas IA and IB are enantiomers (or diastereomers if either $R^1$ or $R^2$ contains a second chiral center) and are chiral because $R^1$ is different in structure or chirality from $R^2$.

In chiral amines of Formulas IA and IB, the amino group is a primary amine and is bound to a secondary carbon atom, i.e., a carbon atom carrying one hydrogen atom and two substituents which are other than hydrogen ($R^1$ and $R^2$). In addition, while $R^1$ and $R^2$ are selected from the same type of structures, these groups must render the molecule chiral; e.g., $R^1$ will be different from $R^2$ in structure or chirality or $R^1$ and $R^2$ when taken together are a chiral group. Generally, when taken independently, $R^1$ and $R^2$ will be alkyl, aralkyl, or aryl groups, preferably a straight or branched alkyl group of from 1 to 6 carbon atoms, a straight or branched phenyl-alkyl group of from 7 to 12 carbon atoms, or a phenyl or naphthyl group. Examples include methyl, ethyl, n-propyl, i-propyl, n-butyl, i-butyl, s-butyl, phenyl, benzyl, phenethyl, 2-phenylpropyl, etc.

Each $R^1$ and $R^2$ group optionally can be substituted with one or more groups, provided the groups do not significantly affect or compete with the action of the omega-transaminase. This can be readily determined by a simple inhibition assay. If inhibition is detected, it often can be minimized by conducting the reaction at lower concentrations of that reactant. Typical substituents without limitation include halo such as chloro, fluoro, bromo and iodo, hydroxy, lower alkyl, lower alkoxy, lower alkylthio, cycloalkyl, carbamoyl, mono- and di-(lower alkyl) substituted carbamoyl, trifluoromethyl, phenyl, nitro, amino, mono- and di-(lower alkyl) substituted amino, alkylsulfonyl, arylsulfonyl, alkylcarboxamido, arylcarboxamido, etc. Typical groups when $R^1$ and $R^2$ are taken together are 2-methylbutane-1,4-diyl, pentane-1, 4-diyl, hexane-1,4-diyl, hexane-1,5-diyl, and 2-methylpentane-1,5-diyl.

Typical amines for which the present process is suitable include without limitation 2-aminobutane, 2-amino-1butanol, 1-amino-1-phenylethane, 1-amino-1-(2-methoxy-5-fluorophenyl)ethane, 1-amino-1-phenylpropane, 1-amino-1-(4hydroxyphenyl)propane, 1-amino-1-(4-bromophenyl) propane, 1-amino-1-(4-nitrophenyl)propane, 1-phenyl-2-aminopro-pane, 1-(3-trifluoromethylphenyl)-2-aminopropane, 2-aminopropanol, 1-amino-1-phenylbutane, 1-phenyl-2-aminobutane, 1-(2,5-di-methoxy-4-methylphenyl)-2-aminobutane, 1-phenyl-3-aminobutane, 1-(4-hydroxyphenyl)-3-aminobutane, 1-amino-2-methylcyclopentane, 1-amino-3-methylcyclopentane, 1-amino-2-methylcyclohexane, 1-amino-1-(2-naphthyl)ethane, 3-methylcyclopentylamine, 2-methylcyclopentylamine, 2-ethylcyclopentylamine, 2-methylcyclohexylamine, and 3-methylcyclohexylamine, 1-aminotetralin, 2-aminotetralin, 2-amino-5-methoxytetralin, and 1-aminoindan.

Thermostable Omega-Transaminases

Any of the thermostable omega-transaminases described above can be used to produce chiral compounds. A thermostable omega-transaminase can be used in free form (e.g., as a purified enzyme or in a cell-free extract). The enzyme optionally can be immobilized on a suitable support or matrix, such as cross-linked dextran or agarose, silica, polyamide, or cellulose. The enzyme also can be encapsulated in polyacrylamide, alginates, fibers, or the like. Methods for such immobilization are described in the literature (see, for example, *Methods in Enzymology* 44, 1976). The latter embodiment is particularly useful because, for example, once the immobilized enzyme is prepared one can simply feed the amino acceptor and a mixture of the chiral amines over the immobilized enzyme in order to effect the desired enrichment, and then remove the formed ketone. See U.S. Pat. Nos. 4,950,606; 5,300,437; and 5,346,828.

Enantiomeric Enrichment of a Chiral Amine

In some embodiments, thermostable omega-transaminases of the invention are used in methods for enantiomeric enrichment of a mixture of chiral amines. "Enantiomeric enrichment" is an increase in the amount of one chiral form compared to the other. This enrichment can involve (i) a decrease in the amount of one chiral form compared with the other, (ii) an increase in the amount of one chiral form compared with the other, or (iii) a decrease in the amount of one chiral form and an increase in the amount of the other chiral form. Enantiomeric enrichment typically is expressed as "enantiomer excess," or "ee," according to the following expression:

$$ee = \frac{E^1 - E^2}{E^1 + E^2} \times 100$$

in which $E^1$ is the amount of the first chiral form of the amine and $E^2$ is the amount of the second chiral form of the same amine. For example, if the initial ratio of the two chiral forms is 50:50 and an enantiomeric enrichment sufficient to produce a final ratio of 50:30 is achieved, the ee with respect to the first chiral form is 25%, whereas if the final ratio is 70:30, the ee with respect to the first chiral form is 40%. Typically with methods of the present invention, an ee of 90, 91, 92, 93, 94, 95, 96, 97, 98, or 99% or greater can be achieved. Enantiomeric enrichment can be determined by any means known in the art. For example, the ee of a given product can be determined by reaction with (−) α-(trifluoromethylphenyl)methoxyacetyl chloride (Gal, *J. Pharm. Sci.* 66, 169, 1977; Mosher et al., *J. Org. Chem.* 34, 25430, 1969) followed by capillary gas chromatography of the derivatized product on a Chrompack fused silica column.

Broadly, methods of enantiomeric enrichment involve subjecting a mixture of chiral amines to the action of a thermostable omega-transaminase of the invention in the presence of an amino acceptor.

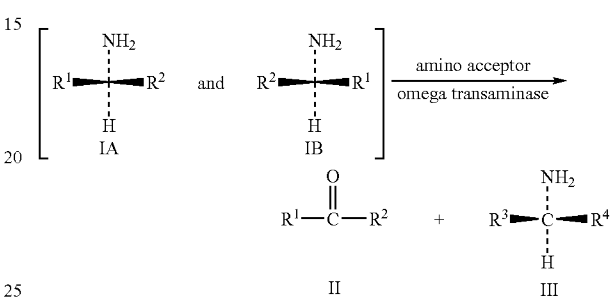

in which $R^1$ and $R^2$ are as defined above and, in Formula III, either $R^3$ is $R^1$ while $R^4$ is $R^2$ or $R^3$ is $R^2$ while $R^4$ is $R^1$.

In general, the enzymatic process operates on only one chiral form, or operates on one chiral form to a far greater extent than the other. Because the reaction is an equilibrium, either the forward or reverse reactions can be favored by adding additional starting materials or removing reaction products. Thus, in an enantiomeric enrichment reaction, additional quantities of the amino acceptor can be added (up to saturation) and/or the ketone formed can be continuously removed from the reaction mixture. Conversely when one stereoselectively synthesizes one chiral form of an amine, as described below, additional ketone can be added (up to saturation) and/or the amine formed can be removed.

When the undesired chiral form of the amine is converted to the ketone and the desired chiral form is not, the latter can be readily isolated by conventional techniques. A partial separation can be effected by acidification, extraction with a hydrocarbon such as heptane to remove the ketone, rendering the aqueous phase basic, and re-extraction with a hydrocarbon such as heptane. When, on the other hand, both chiral forms of the amine are desired, the form which is converted to the ketone can be removed from the reaction mixture (or from the aqueous phase in a two phase mixture) and independently subjected to the action of an omega-transaminase in the presence of a amino donor to generate the same chiral form which was initially converted to the ketone.

Stereoselective Synthesis of a Chiral Form

Thermostable omega-transaminases of the invention also can be used in methods of stereoselective synthesis, i.e., to preferentially synthesize one chiral form of an amine of formula IA or IB in an amount substantially greater than the other. These methods typically involve subjecting a ketone of the formula:

II

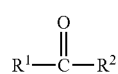

in which $R^1$ and $R^2$ are as defined above to the action of a thermostable omega-transaminase of the invention in the presence of an amino donor until a substantial amount of one of the chiral amines is formed. "Substantially greater" as used herein refers to a percentage of the combined amount of both chiral forms of at least about 51% (e.g., at least 51, 55, 60, 65, 70 75, 80, 85, 90, 91, 92, 93, 94, 95, 96, 97, 98, or 99%).

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

EXAMPLE 1

Stereoselective Synthesis and Enantiomeric Enrichment Reactions

To assess activity of a thermostable omega-transaminase in a stereoselective synthesis reaction, 108.8 g potassium phosphate is added to water in a reactor. One liter of concentrated HCl is added, and then isopropylamine is added. The pH is adjusted to 7-7.4, and the volume is adjusted to 8 L (i.e., 100 mM potassium phosphate and 1.0 M isopropylamine). Pyridoxal-5-phosphate is added to a final concentration of 2 mM, followed by 1-5 g of spray-dried crude thermostable omega-transaminase. Preferably the reaction takes place in the absence or near absence of oxygen, so nitrogen flow is started to purge the reaction mixture of oxygen. The enzyme is mixed for one hour under a nitrogen atmosphere, pH adjusted to 7-7.2, and the reaction is started by adding ketone 7-methoxy-2-tetralone to a final concentration of 100 mM. Samples are taken at regular intervals. Stability and activity are measured by monitoring the formation of amine product for at least 10 hours. FIG. 1 shows the typical progress of a synthesis reaction using the enzyme CNB03-03.

To assess activity of a thermostable omega-transaminase in an enantiomeric enrichment reaction, racemic methylbenzylamine is used as the amine donor, and sodium pyruvate is used as the amine acceptor; the rest of the components are the same.

EXAMPLE 2

Identification of Thermostable Transaminases

"CHIR-9867" (SEQ ID NO:6) is a mutant, thermostable transaminase. Mutants of CHIR-9867 were generated using error-prone PCR (Leung et al., *J. Methods Cell. Mol. Biol.* 1, 11-15, 1989) and screened for their activity at 60-68° C. compared to CHIR-9867 on a plate screen for the synthesis of S-7-Methoxy-2-aminotetralin (S7MAT). The plate screen is performed by subjecting the mutants to a reaction whereby an amine is converted into a ketone that becomes colored in the presence of oxygen. The rate at which the color is formed is used as an indication of the activity of the enzyme.

Thirty-eight potential candidates were identified from a primary plate screen. All identified mutants were further screened on plates, and thirteen mutants were identified as potential improved mutants. These 38 mutants appeared to have a better rate than the wild-type enzyme. These thirteen mutants were screened on 3 mL scale (reaction volume was 3 mL) at ≈65° C. The three best mutants were identified and named CNB03-01, CNB03-02, CNB03-03. These three identified mutants were further screened on 40 mL scale under a nitrogen atmosphere at different temperatures and enzyme concentrations to select the mutant with the best reaction rate. The reaction rate of CHIR-9867 was used as a control. The results obtained from the 40 mL scale screening are shown in Table 3.

TABLE 3

| Enzyme # | Quantity (g/L) | Reaction Conditions | Initial Rate (mM/hr) |
|---|---|---|---|
| CNB 03-01 | 15 | 160 mM ketone, 650 mM donor amine, 60-62° C. | 68 |
| CNB 03-02 | 15 | 160 mM ketone, 650 mM donor amine, 60-62° C. | 58 |
| CNB 03-03 | 15 | 160 mM ketone, 650 mM donor amine, 60-62° C. | 71 |
| CHIR-9867 | 15 | 160 mM ketone, 650 mM donor amine, 60-62° C. | 28 |

All mutants showed high selectivity and the amine was synthesized with an ee>99%. Chiral purity was measured using HPLC with a chiral column.

CNB 03-01, CNB 03-02, and CNB 03-03 were sequenced. Their amino acid sequences are shown in SEQ ID NOS:8, 10, and 12, respectively. As expected, all of these mutant transaminases were altered in amino acid sequence compared to the amino acid sequence of CHIR-9867 (SEQ ID NO:6) from which they were generated. The changes in amino acid sequences between CNB 03-01, CNB 03-02, CNB 03-03, and CHIR-9867 are shown in Table 2.

EXAMPLE 3

Summary of HPLC Analytical Methods used for Chemical and Chiral Analysis

| HPLC Method for Chemical Analysis | |
|---|---|
| Column: | Waters, Nova-Pak Phenyl RCM 0.8 cm × 10 cm × 4 μm |
| Mobile Phase: | 25/75 (v/v-premixed) isopropanol/water containing 0.15% $H_3PO_4$ and 10 mM sodium octanesulfonate |
| Flow Rate: | 1.5 ml/min |
| Injection Volume: | 10 μL |
| Temperature: | Ambient |
| Run Time: | 20 min |
| Detection: | UV @ 254 nm |
| Typical Retention times: | ketone, 9-10 min; amine 13-14 min |

| HPLC Method for Chiral Analysis | |
|---|---|
| Column: | Diacel Crownpak CR (+) 15 cm × 0.40 cm × 5 μm |
| Mobile Phase: | 15/85 (v/v-premixed) methanol/1% $HClO_4$ in water. |
| Flow Rate: | 1.25 ml/min |
| Injection Volume: | 15 μL |
| Temperature: | 40° C. |
| Run Time: | 50 min |
| Detection: | UV @ 220 nm |
| Typical Retention Times: | R-amine 20-21 minutes; S-amine, 24-25 min. |

EXAMPLE 4

Generation of a New Enzymes, CNB04-01, with Extended Thermostability

"CNB03-03" (SEQ ID NO:10) is a mutant, thermostable transaminase. Mutants of CNB03-03 were generated using error-prone PCR (Leung et al., *J. Methods Cell. Mol. Biol.* 1, 11-15, 1989) and screened for their activity after more than 24 hours at 60-68° C. compared to CNB03-03 on a plate screen for the synthesis of S-7-Methoxy-2-aminotetralin (S7MAT). The plate screen was performed by subjecting the mutants to a reaction whereby an amine is converted into a ketone that becomes colored in the presence of oxygen. The rate at which the color is formed was used as an indication of the activity of the enzyme.

Thermostability of CNB04-01 was tested as follows: enzyme was kept at 50° C. in a solution of 100 mM calcium chloride, 100 mM sodium acetate, 1 mM pyridoxal-5-phosphate at pH 8.5 (0.1 gram enzyme dissolved in 10 ml of solution). Periodically, 1 ml samples were withdrawn and added to 20 ml of reaction mixture pH 8.5 and incubated at 50° C. The change on (S)-aminotransferase activity as a function of time was measured. Results showed that the activity of the enzyme remained relatively stable for over a period of 150 hours with the initial rate at time zero of ~36 mM/hour and an initial rate of ~25 mM/hour after 150 hours.

EXAMPLE 5

Initial rates of activity of CNB05-01 (SEQ ID NO:16) and CNB05-02 (SEQ ID NO:18)

The initial rates of activity of the thermostable transaminases CNB05-01 (SEQ ID NO:16) and CNB05-02 (SEQ ID NO:18) were tested under the following reaction conditions: V=50 ml [2 mM PLP, 0.5 IPA, 200 mM sodium acetate], Enzyme: 5 g/l; (pH)0=7, ketone=130 mM, 55° C.

Figure 2:
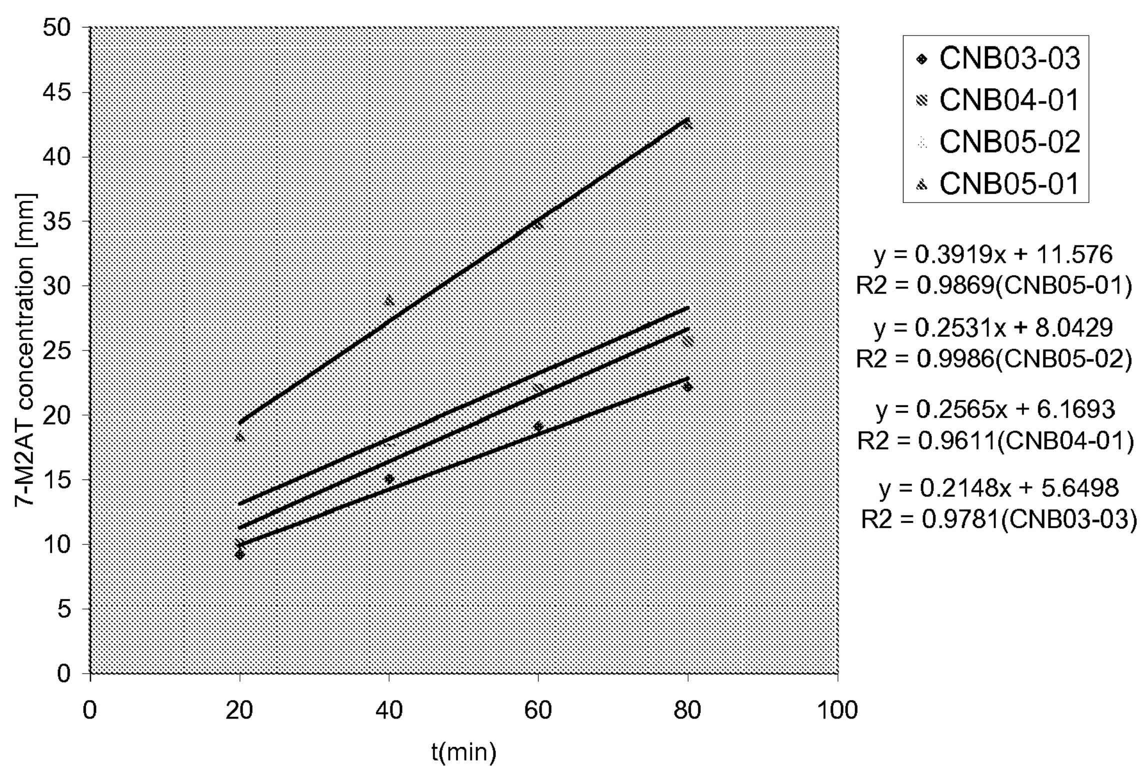
FIG. 2. Graph showing initial rates of activity of mutants CNB05-01 (SEQ ID NO:16) and CNB05-02 (SEQ ID NO:18).

The results are shown in FIG. 2. From FIG. 2 it is clear that the initial rate of CNB05-01 and CNB05-02 is greater than CNB03-03. The initial rate of CNB05-01 was better than all the enzymes tested and was 0.39 mM/minute under the conditions tested (CNB03-03 had an initial rate of 0.21 mM/minutes).

EXAMPLE 6

Comparison of Enzymatic Activity of CNB05-01 (SEQ ID NO:16) and CNB03-03 (SEQ ID NO:12)

Enzymatic activity of the thermostable transaminases CNB05-01 (SEQ ID NO:16) and CNB03-03 (SEQ ID NO:12) were tested under the following conditions: 55° C., pH 7 (0-5 hr), 100 ml/min N2, 0.75 M IPA, 2 mM PLP, 200 mM sodium acetate, 2 ml ketone (130 mM), V=100 ml, nitrogen flow surface 100 ml/min.

Figure 3A:
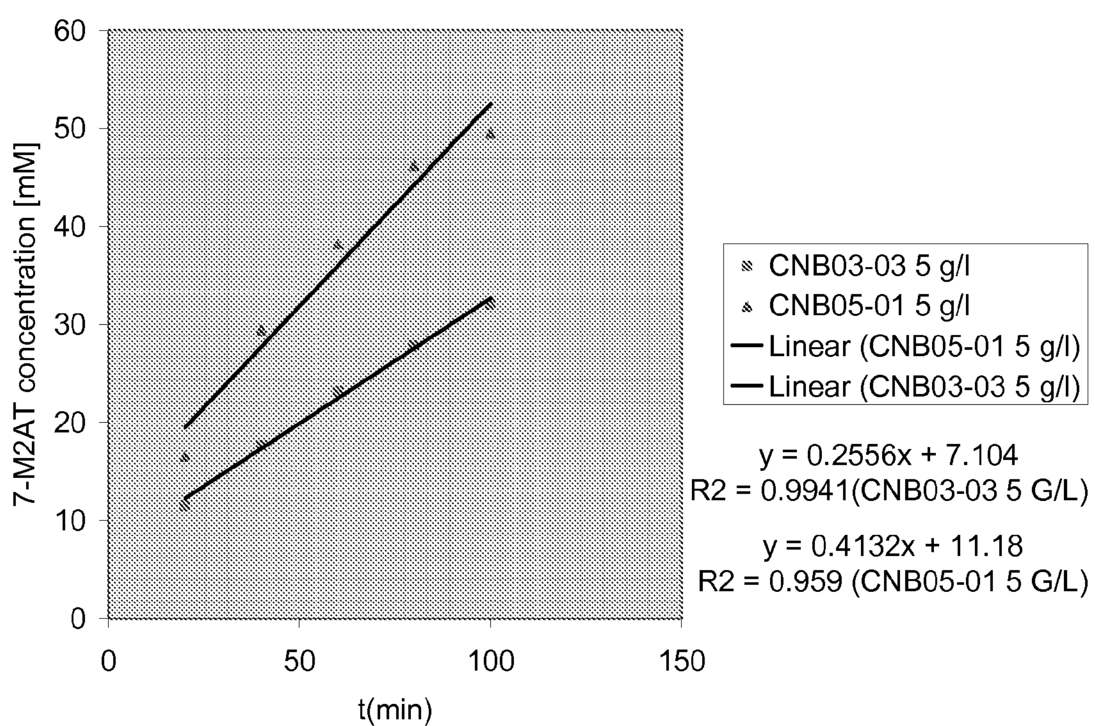
FIGS. 3A-B. Graphs showing relative enzyme activities of CNB05-01 (SEQ ID NO:16) and CNB03-03 (SEQ ID NO:12).
Figure 3B:
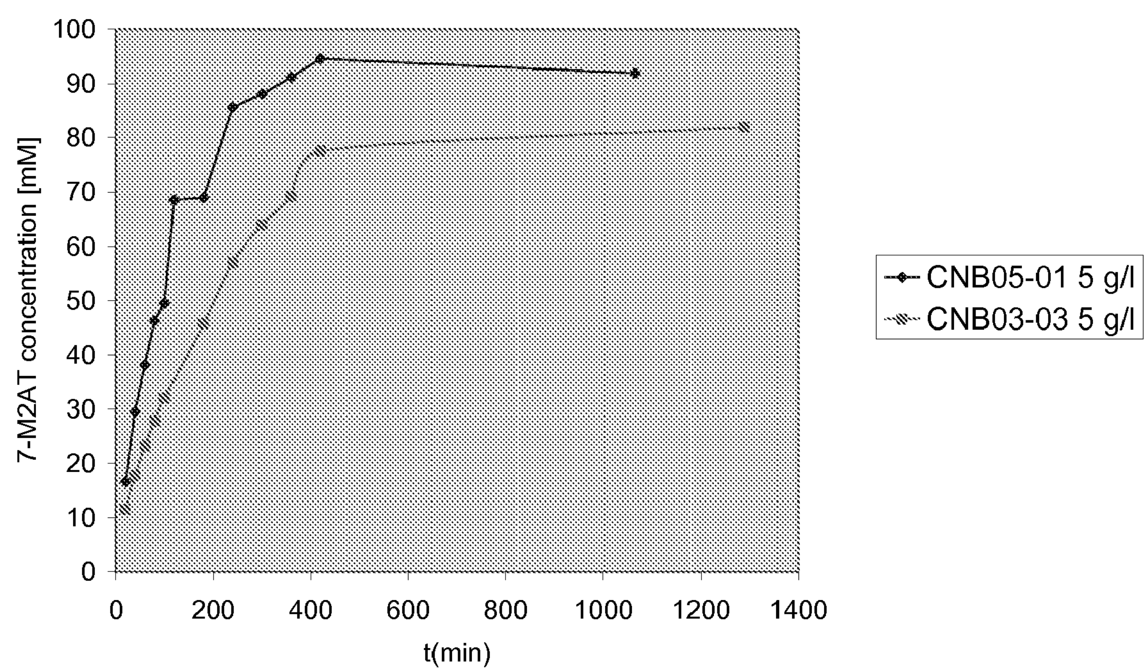

The results are shown in FIGS. 3A and 3B. FIG. 3A demonstrates reproducibility of the results described in this example with the initial rate of CNB05-01 at 0.41 mM/minute and CNB03-03 at 0.25 mM/minute. FIG. 3B shows the results obtained during the course of the reaction with CNB05-01 achieving a higher conversion in a shorter period of time by virtue of having a higher initial rate.

The invention claimed is:

1. An isolated thermostable omega transaminase which comprises the amino acid sequence SEQ ID NO:8.

2. An isolated polynucleotide which encodes the amino acid sequence SEQ ID NO:8.

3. The isolated polynucleotide of claim 2 which comprises the nucleotide sequence SEQ ID NO:7.

4. The isolated polynucleotide of claim 2 which is an expression construct.

5. A method for enantiomeric enrichment of a mixture of two enantiomeric chiral amines comprising contacting:

(a) a mixture comprising a first chiral amine and a second chiral amine which is an enantiomer of the first chiral amine, wherein the first chiral amine has the structural formula:

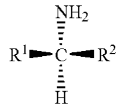

and wherein the second chiral amine has the structural formula:

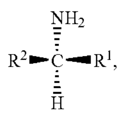

wherein each of $R^1$ and $R^2$, when taken independently, is alkyl, arylalkyl, or aryl and may be unsubstituted or substituted with one or more enzymatically non-inhibiting groups, and wherein $R^1$ and $R^2$ render the molecule chiral;

(b) a thermostable omega transaminase which comprises the amino acid sequence SEQ ID NO:8; and (c) an amino acceptor for a time sufficient to convert the first chiral amine to a ketone such that the amount of the second chiral amine in the mixture is at least about 90% relative to the amount of the first chiral amine.

6. The method of claim 5 wherein the contact is maintained at least until the amount of the second chiral amine in the mixture is at least about 99% relative to the amount of the first chiral amine.

7. The method of claim 5 wherein the one or more enzymatically non-inhibiting groups are selected from the group consisting of halogen, hydroxy, lower alkyl, lower alkoxy, lower alkylthio, cycloalkyl, carbamoyl, mono-(lower alkyl)-substituted carbamoyl, di-(lower alkyl)-substituted carbamoyl, trifluoromethyl, phenyl, nitro, amino, mono-(lower alkyl) substituted amino, di-(lower alkyl) substituted amino, alkylsulfonyl, arylsulfonyl, alkylcarboxamido, arylcarboxamido, 2-methylbutane-1,4-diyl, pentane-1,4-diyl, hexane-1,4-diyl, hexane-1,5-diyl, and 2-methylpentane-1,5-diyl.

8. The method of claim 5 wherein the amino acceptor is a ketocarboxylic acid.

9. The method of claim 8 wherein the ketocarboxylic acid is selected from the group consisting of glyoxalic acid, pyruvic acid, oxaloacetic acid, and salts thereof.

10. The method of claim 5 wherein the amino acceptor is selected from the group consisting of oxaloacetic acid and pyruvic acid.

11. A method for stereoselective synthesis of one of two chiral forms of an amine comprising contacting:

(a) a ketone having the structural formula:

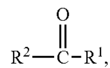

II wherein each of $R^1$ and $R^2$, when taken independently, is alkyl, arylalkyl, or aryl and may be unsubstituted or substituted with one or more enzymatically non-inhibiting groups;

(b) a thermostable omega transaminase which comprises the amino acid sequence SEQ ID NO:8; and (c) an amino donor for a time sufficient to form a substantially greater amount of a first chiral form of the amine than the amount of a second chiral form of the amine.

12. The method of claim 11 wherein the one or more enzymatically non-inhibiting groups are selected from the group consisting of halogen, hydroxy, lower alkyl, lower alkoxy, lower alkylthio, cycloalkyl, carbamoyl, mono-(lower alkyl)-substituted carbamoyl, di-(lower alkyl)-substituted carbamoyl, trifluoromethyl, phenyl, nitro, amino, mono-(lower alkyl) substituted amino, di-(lower alkyl) substituted amino, alkylsulfonyl, arylsulfonyl, alkylcarboxamido, arylcarboxamido, 2-methylbutane-1,4-diyl, pentane-1,4-diyl, hexane-1,4-diyl, hexane-1,5-diyl, and 2-methylpentane-1,5-diyl.

13. The method of claim 11 wherein the amino donor is selected from the group consisting of glycine, L-alanine, L-aspartic acid, S-2-aminobutane, propyl amine, and benzyl amine.

* * * * *